United States Patent
Brentani et al.

(10) Patent No.: US 6,350,854 B1
(45) Date of Patent: *Feb. 26, 2002

(54) ISOLATED 55 TO 72 KDA PROTEIN WHICH BINDS TO PRION PROTEINS

(75) Inventors: Ricardo R. Brentani; Vilma J. Martins; Sandro J. de Souza, all of Sao Paulo (BR)

(73) Assignees: Ludwig Institute for Cancer Research, New York, NY (US); Fundacao Antonio Prudente, Sao Paulo (BR)

(*) Notice: Subject to any disclaimer, the term of this patent is extended or adjusted under 35 U.S.C. 154(b) by 0 days.

This patent is subject to a terminal disclaimer.

(21) Appl. No.: 09/528,023

(22) Filed: Mar. 17, 2000

Related U.S. Application Data

(60) Division of application No. 08/948,706, filed as application No. PCT/US96/05028 on Apr. 11, 1996, now Pat. No. 6,066,320, which is a continuation-in-part of application No. 08/421,059, filed on Apr. 12, 1995, now Pat. No. 5,679,530.

(51) Int. Cl.[7] ........................ A61K 38/00; A61K 39/00; C12Q 3/00; G01N 33/53; C07K 16/00
(52) U.S. Cl. ................. 530/326; 424/185.1; 424/186.1; 424/193.1; 424/204.1; 424/139.1; 435/4; 435/7.1; 530/387.1; 530/350; 530/388.2; 530/388.3; 530/826
(58) Field of Search ........................ 424/139.1, 185.1, 424/186.1, 193.1, 204.1; 435/4, 7.1; 530/326, 350, 387.1, 388.2, 388.3, 826

(56) References Cited

U.S. PATENT DOCUMENTS 5,679,530 A * 10/1997 Brentani et al.

OTHER PUBLICATIONS

Brentani, "Biological Implications of Complementary Hydropathy of Amino Acids," *J. Theor. Biol.*, 133:495–499 (1988).
Brentani, "Complementary Hydropathy and the Evolution of Interactive Polypeptides," *J. Mol. Evol.*, 31:239–243 (1990).
Goldgaber, "Anticipating the Anti–Prion Protein?", *Nature*, 351:106 (1991).
Manson et al., "Anti–Prions and Other Agents," *Nature*, 352:291 (Jul. 25, 1991).
Hewinson et al., "Anti–Prions and Other Agents," *Nature*, 352:291 (Jul. 25, 1991).
Bendheim et al., "Anti–Prions and Other Agents," *Nature*, 352:291–292 (Jul. 25, 1991).
Moser et al., "An Anti–Prion Protein?", *Nature*, 362:213–214 (Mar. 18, 1993).
Forloni et al., "Neurotoxicity of a Prion Protein Fragment," *Nature*, 362:543–546 (Apr. 8, 1993).
Elton et al., "Purification of An Angiotensin II Binding Protein By Using Antibodies to a Peptide Encoded by Angiotensin II Complementary RNA," *Proc. Natl. Acad. Sci. USA*, 85:2518–2522 (Apr. 1988).
Ghiso et al., "Binding of Cystatin C to C4: The Importance of Sense—Antisense Peptides in Their Interaction," *Proc. Natl. Acad. Sci. USA*, 87:1288–1291 (1990).
Sigma Chemical Catalog, see page 1598 (1993).

* cited by examiner

Primary Examiner—Hankyel T. Park
Assistant Examiner—Stacy S. Brown
(74) Attorney, Agent, or Firm—Fulbright & Jaworski

(57) ABSTRACT

The invention involves an isolated anti-prion-protein binding protein that has a molecular weight of about 55 kD to about 72 kD as determined by SDS-PAGE. Also described is a peptide derived from this isolated anti-prion-protein binding protein. Diagnostic uses for each of these molecules are discussed.

2 Claims, 7 Drawing Sheets

```
                         SEQUENCE LISTING (1) GENERAL INFORMATION:

(iii) NUMBER OF SEQUENCES:  1

(2) INFORMATION FOR SEQ ID NO:1:

(i) SEQUENCE CHARACTERISTICS:
          (A) LENGTH: 17
          (B) TYPE:  amino acid
          (C) STRANDEDNESS: single
          (D) TOPOLOGY: linear (xi) SEQUENCE DESCRIPTION:  SEQ ID NO: 1:

Tyr His Val Ala Thr Lys Ala Pro His His Gly Pro Cys Arg Ser Ser
1               5                   10                  15

Ala
```

ISOLATED 55 TO 72 KDA PROTEIN WHICH BINDS TO PRION PROTEINS

RELATED APPLICATIONS

This application is a divisional application of Ser. No. 08/948,706 filed May 26, 1998, now U.S. Pat. No. 6,066,320, which is the national stage entry of PCT/US96/05028 filed Apr. 11, 1996, which is a C-I-P of U.S. application Ser. No. 08/421,059 filed Apr. 12, 1995, now U.S. Pat. No. 5,679,530, and incorporated by reference.

FIELD OF THE INVENTION

This invention relates to the identification and isolation of proteins which bind with prion protein, referred to hereafter as PrP. More particularly, the isolated proteins of the invention has a molecular weight of from about 55 kD to about 72 kD as determined by SDS-PAGE, and are referred to hereafter as anti-PrP proteins or PrP binding protein. Also described is an isolated peptide consisting of an amino acid sequence from said binding protein/antiPrP protein. Both the peptide and the protein have various diagnostic efficacies. In the case of the peptide, it can be used, e.g., to produce antibodies which are in turn used to identify the anti-PrP protein. Also, the peptide can bind, itself, to PrP. Similarly, the full protein may be used in the same way. Various diseases associated with prions can thus be diagnosed or screened using these materials. Further, one can screen for the presence of PrP in a sample using the protein of the invention.

BACKGROUND AND PRIOR ART

"Prions" or "protein infectious particles", have been implicated in a number of pathological conditions. Known prion associated diseases are referred to generally as spongiform encephalopathies, due to a common feature of the diseases, i.e., the formation of "holes" in cranial tissue.

By far the most commonly recognized disease associated with prions is "scrapie", found in sheeps and goats. Afflicted animals lose coordination, and eventually become unable to stand. Additional animal disorders associated with prions include transmissible mink encephalopathy; chronic wasting disease of mule, deer and elk; feline spongiform encephalopathy; and bovine spongiform encephalopathy ("mad cow disease"). Among humans, Kuru, or "laughing death" has been associated with cannibalism. By far the most serious human disorder associated with prions, however, is Creutzfeldt-Jakob disease. This condition generally becomes evident via the development of dementia in the subject. It is a cause of great concern because it can be transmitted iatrogenically, such as by corneal transplantation, use of contaminated surgical instruments, injection of purified growth hormones or other pituitary based materials, as well as via implantation of dura mater or electrodes in the brain. Additional pathological conditions associated with prions include Gerstmann-Str aussler-Scheinker disease (lataxia and cerebellum damage), and fatal familial insomnia. Both of these conditions are inheritable, and typically appear in midlife.

At first, the aforementioned conditions were believed to be caused by a slow acting virus found in cerebral tissue. This hypothesis was based upon the observation that the diseases could be transmitted by injection of brain extracts of afflicted animals into healthy animals. This hypothesis, however, is generally no longer accepted, because a virus has not been isolated in spite of concerted efforts to do so.

What has been found about these conditions is that, although inheritable, they are caused by proteinaceous material, rather than by nucleic acids. The proteinaceous material is referred to as the prion. Among the experiments which led to the hypothesis that protein material was implicated was the treatment of materials from infected animals to inactivate proteins but not nucleic acids. Under these conditions, the disease was not transmitted.

Elaborations on this hypothesis have identified a single protein in scrapie prions. This protein, "prion protein", will be referred to as—PrP—hereafter. It is used, generically, to refer to the protein which forms the prion. See, e.g., Prusener, Science 252: 1512–1522 (Jun. 14, 1991) ("Molecular Biology of Prion Diseases"); Prusiner, et al, ed., *Prion Diseases of Humans And Animals* (Ellis Horwood, 1992).

As with all proteins, PrP is encoded by a gene; however, expression of PrP is not sufficient to cause a prion associated condition. It has been determined that PrP may undergo changes in its three dimensional structure, leading to its prion form. To elaborate, the benign form of PrP shows a multiple alpha helix geometry. In the form of infective prions, however, the three dimensional structure "elongates", forming beta sheets. In summary, the difference between the normal, harmless form of PrP and the form associated with diseases, e.g., appears to be completely conformational.

"Complementary hydropathy", a concept critical to understanding the invention described herein, was first suggested by Biro, Medical Hypothesis 7: 981 (1981). The concept Biro set forth was based upon an observation that protein/protein interactions were observed to be specific. He argued that complementary coding, i.e., coding by both sense and "anti-sense" strands of nucleic acid molecules could lead to the required specificity. Work on the interaction between ACTH, γ-endorphin, angiotensin II, luteinizing hormone release hormone, and fibronectin, and their receptors, supports this hypothesis. See Bost, et al, Mol. Cell Endocrin 44:1 (1986) (ACTH); Carr, et al, J. Neuroimmunol 12: 329 (1986) (γ-endorphin), Elton, et al, Proc. Natl. Acad. Sci. USA 85: 2518 (1988); (angiotensin II); Mulchahey, et al, Proc. Natl. Acad. Sci. USA 83: 9714 (1986) (luteinizing hormone-releasing hormone); and Brentani, et al, Proc. Natl. Acad. Sci. USA 85: 364 (1988) (fibronectin).

All of this work supported a concept hypothesized by Blalock, et al, Biochem. Biophys. Res. Commun. 121: 203 (1984). Their observation was that when the codons for hydropathic amino acids were compared to their complementary codons, these complementary codons were generally codons which code hydrophilic amino acids. Blalock, et al observed a significant correlation (r=0.74) between hydropathic coefficients of amino acids encoded for by opposing DNA strands, and thus postulated that peptides encoded by complementary DNA strands would bind one another. As indicated, supra, this hypothesis is supported for a number of peptides.

In 1991, Goldgaber, Nature 351: 106 (May 9, 1991), reported on the possible application of complementarily to PrP. Goldgaber reported analyzing PrP complementary DNA sequences, and the identification of a large, overlapping open reading frame in the DNA "antisense" strand for the PrP gene. When Goldgaber analyzed the deduced amino acid sequence for this complementary coding region, he found it to be nearly a mirror image of PrP. Goldgaber is incorporated by reference in its entirety. While Manson, et al, Nature 352: 291 (Jul. 25, 1991), questioned this work, Hewinson, et al, Nature 352: 291 (Jul. 25, 1991) noted that it confirmed their own work. Prusiner, et al, Nature 362: 213 (Mar. 3, 1993), provided an interesting "wrinkle" on this research, when they reported that they did find an RNA unit of the proper size (4.5 kb) for hybridizing to PrP sense strands, but it was not derived from the antisense PrP strand.

The reports discussed supra, as well as a report by Moser, et al, Nature 362: 213 (Mar. 18, 1993), discuss the possibility of the anti-PrP protein, as it will be referred to hereafter, in prion associated diseases. Hewinson, et al suggested that the complementary protein might be a PrP receptor.

The work which follows presents, for the first time, the identification and characterization of an anti-PrP binding protein. This material may be used to identify the presence of PrP in samples, thus providing a method of screening and/or diagnosis, especially when other symptoms characteristic of prion associated disorder are observed. In view of the prevalence of prion associated disorders in livestock, e.g., there are both human and veterinary uses for the invention.

BRIEF DESCRIPTION OF THE FIGURES

In FIG. 3A, the binding of labelled antibodies to cells is shown. FIG. 3B shows localization of the binding.

DETAILED DESCRIPTION OF PREFERRED EMBODIMENTS

EXAMPLE 1

In order to approach the question of whether an anti-prion protein exists, a peptide was synthesized, based upon the work of Forloni, et al, Nature 362: 543–546 (1993), the disclosure of which is incorporated by reference in its entirety. Forloni et al disclose prion peptide "PrP 106–126", which induced cell death in primary rat hippocampal cultures. The peptide, which was used herein, i.e.:
Tyr His Val Ala Thr Lys Ala Pro His His Gly Pro Cys Arg Ser Ser Ala (SEQ ID NO: 1)
is complementary to a peptide derived from PrP, and is itself derived from complementary amino acids 113–129 of a deduced anti-prion ORF, supra.

The synthesized peptide was coupled to Keyhole limpet hemocyanin (KLH), to produce an immunogen. The immunogen was then injected into mice, intraperitoneally, at two week intervals, to a total of 100 ug of total protein. After the fourth injection, animals were bled, and titered against uncoupled peptide, via a standard ELISA.

EXAMPLE 2

Once the antiserum was made, it was utilized in immunofluorescence studies. Murine neuroblastoma cell line "neuro 2A" was used. Samples of the cell line were plated ($2\times10^6$ cells/well), in eight well tissue culture chamber slides. The cells were incubated, overnight, after which the slides were washed and the cells fixed with 1% glutaraldehyde. After fixing, a 1:20 horse serum solution was added, for 1 hour at 37° C. A wash with phosphate buffered saline (PBS) followed, and then the antiserum was added, for a period of 2 hours. Following this, the cells were washed extensively, after which a second antibody, i.e., anti-IgG, coupled to fluorescein isothiocyanate, diluted 1:80 in Evan's blue, was added, for 1 hour. Extensive washing followed, after which the slides were mounted, and observed.

Figure 1:
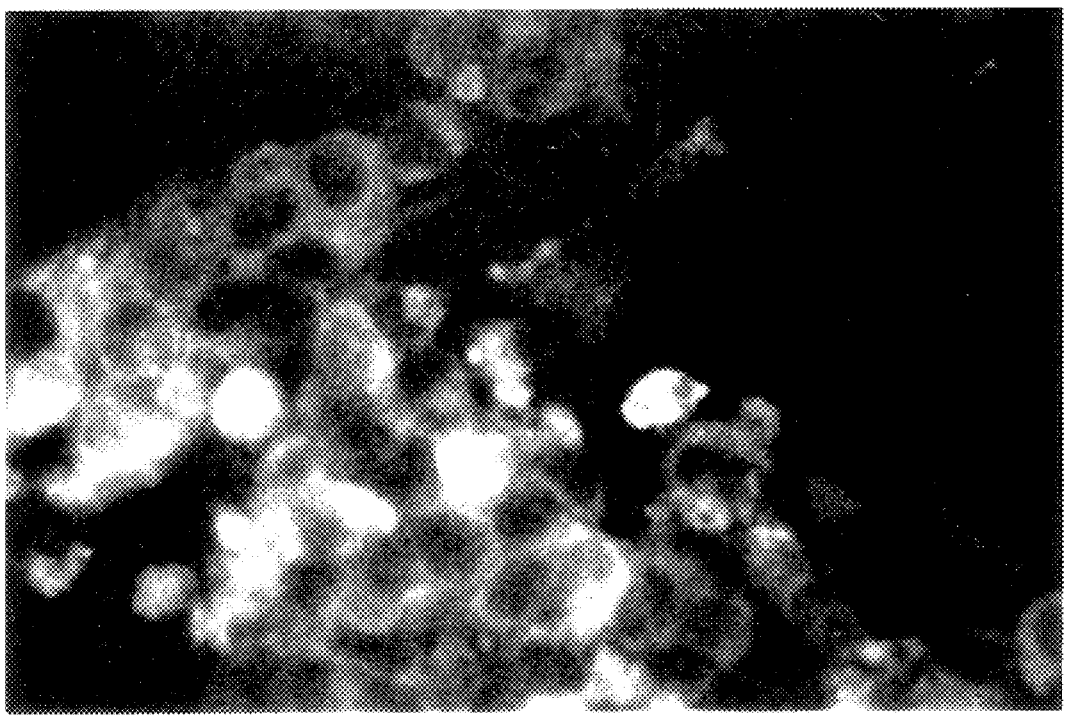
FIG. 1 shows the results of an immunofluorescence assay, using antibodies produced with the peptide of the invention.

FIG. 1 shows these results, although black and white reproduction does not show very clearly the fact that FITC labelling did in fact take place (a green color shows that the labelling did take place). The results do show that the antiserum recognized the surface of the neuro 2A cells. The total reactivity was about 15% of the total population. This result is analogous to results obtained by Butler, et al, J. Virol 62: 1558–1564 (1988), who showed that prp$^{SC}$ infectability in neuro 2A cells was restricted to only certain cells in the population. The observation reported herein suggested the next set of experiments, designed to analyze any possible differences between negative and positive cells.

EXAMPLE 3

In these experiments, positive and negative cells were first cloned by limiting dilution. The positive cells derived from clone "IEI2" and the negative cells from clone "IC4".

Living cells of each clone were surface labelled with $^{125}$I, using the well known lactoperoxidase method. Following labelling, the cells were lysed, and the resulting extracts were incubated with prion peptide PrP$^{106-126}$ coupled to CNBr 4B Sepharose beads overnight, with agitation.

Following the incubation, all bound material (i.e., anything binding to the PrP$^{106-126}$ peptide), was subjected to SDS-PAGE. To carry this out, the bound materials were separated, using a 40% stacking gel, and a 7.5% resolving gel. Proteins were then transferred to nitrocellulose filters (0.45 um pore size), and were then stained, with 0.5% Ponceau S, to verify extent of transfer.

Figure 2:
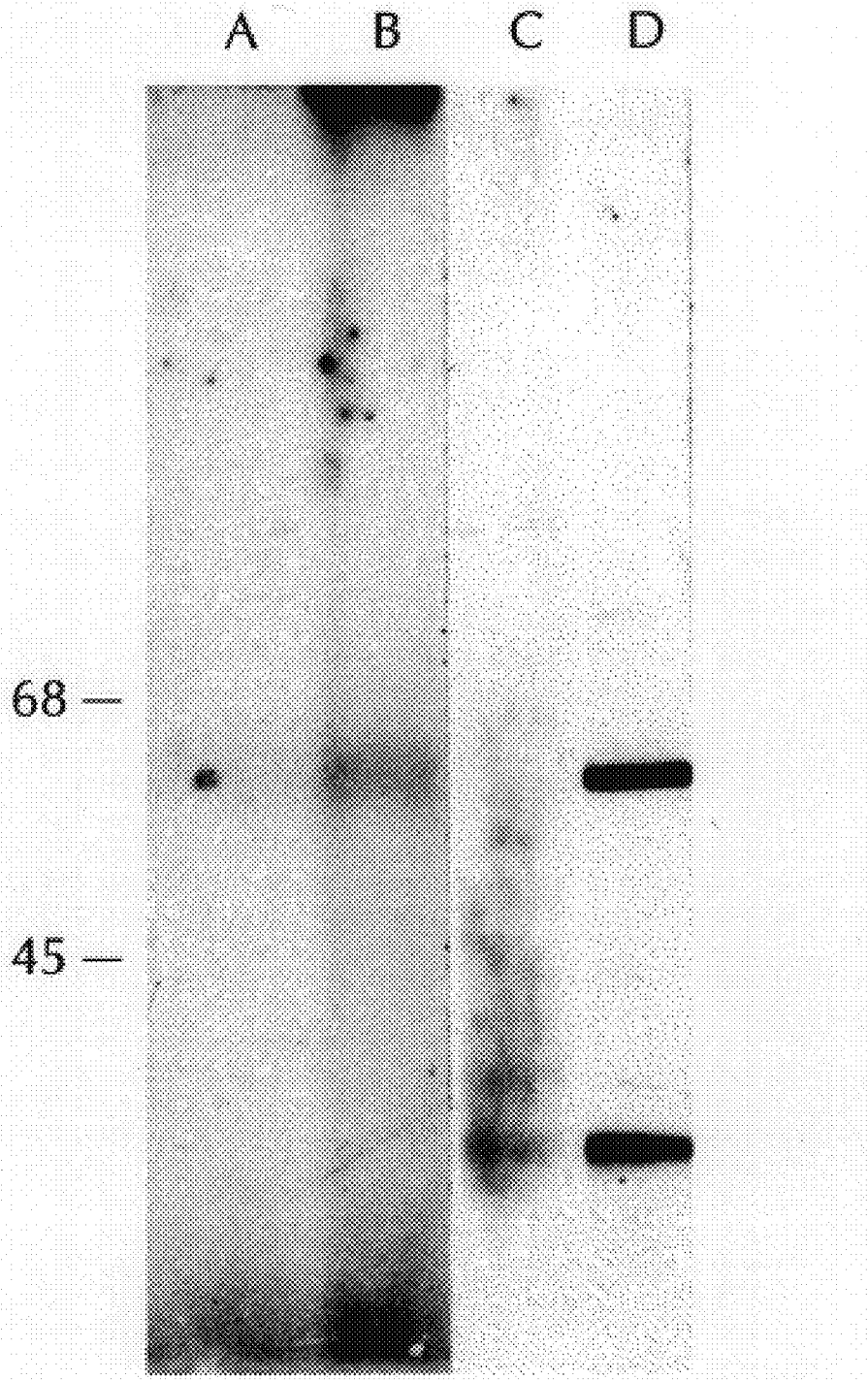
FIG. 2 depicts analyses on SDS-PAGE. In lane A, eluates from cells which were negative in the immunofluorescence assay are presented. Lane B was obtained using eluates from positive cells. Lane C is a Western blot of an eluate of lane B, using normal mouse serum, while lane D resulted from testing such an eluate with the antiserum obtained using the peptide of the invention.

FIG. 2 presents these results. Lane A is from the negative clone, and lane B from the positive clone. The eluates, when compared, revealed that a band for a protein of about 55–65 kD from the positive clones, was not found at a high level with the negative clones. In order to confirm this result, a Western blot was then carried out, as described below.

EXAMPLE 4

Cells from the positive clone were treated, as in example 1, but were not labelled. Also as in Example 3, the unlabelled protein extract was incubated with the PrP$^{106-126}$ Sepharose beads, and bound protein was then eluted and applied to filters, also as described. For the Western blots, the filters were blocked with 5% fat dry milk in PBS, and then incubated with either normal mouse serum, or the antiserum described supra, and then goat anti-mouse biotin conjugated antibody. This labelled antibody was added for 1 hour at room temperature. After extensive washing, the antibodies were developed, using a well known ECL chemiluminescent system. The results are depicted in lanes C–D of FIG. 2, with lane C obtained using normal serum, and lane D the antiserum against anti-prion peptide described supra. The findings suggest that the antiserum against anti-prion peptide recognizes the PrP$^{106-126}$ binding band.

EXAMPLE 5

The examples set forth supra include analysis of co-cultures of neurons and glial cells. The possibility of glial cell labelling could not be discounted, and thus, a protocol was developed to test this possibility.

Glial cells were grown, in culture, using standard methodologies. The cultured cells were then lysed, and extracts were used in Western blot analyses, using the antiserum described supra. The glial cells were completely negative, as compared to the results which are depicted in FIG. 1. One may infer from this that the target of the antiserum is a molecule on neurons, i.e., it is a nerve cell antigen.

EXAMPLE 6

Neuronal cells from the mesencephalon of 14 day old Swiss mice embryos were prepared, in accordance with Mouro Neto, et al, EMBO J 2: 1243–1248 (1983), incorporated by reference. These cells were placed onto 10 mm diameter glass coverslips which had been coated previously with polyornithine (MW: 41 kD; 1.5 ug/ul), in a mixture of DMEM and F12 media, augmented with glucose, glutamine, sodium bicarbonate, and 10% fetal calf serum. See Garcia-Abreu, Neuros. Res. 40: 471–477 (1995), in this regard. After 24 hours, extensive neuromal development could be seen.

Murine antiserum, raised against an amino acid sequence consisting of all but the N-terminal Tyr of SEQ ID NO: 1, and prepared as described, supra, were added at 1:100 v/v, so as to bind to living cells, in accordance with Halftler et al., Eur. J. Neurosci 1: 297–308 (1989). After one hour of incubation, any excess antiserum was removed, and the cells were fixed with 4% paraformaldehyde in 0.1M phosphate buffer, pH 7.6 for 30 minutes. Cells were washed rapidly with 0.1% Triton X-100 in PBS, and incubated overnight with a monoclonal antibody against β-tubulin III, diluted 1:100. Incubation with antibodies labelled with FITC and RITC for two hours followed. Cover slips were then mounted in glycerol-propylgallate/PBS (9:1, v/v). The slides were then observed on a Zeiss, axioplan microscope, with an epi-fluorescence attachment.

Figure 3A:
FIGS. 3A and 3B present data on immunofluorescence assays on murine mesencephalic neurons.

FIG. 3A shows that the antibodies reacted with all murine neuron cells, which is consistent with recognition of a prion receptor/binding protein, expressed by neuron cells. The identify of the cells as neurons was verified by staining with the mAbs to β-tubulin III.

Figure 3B:
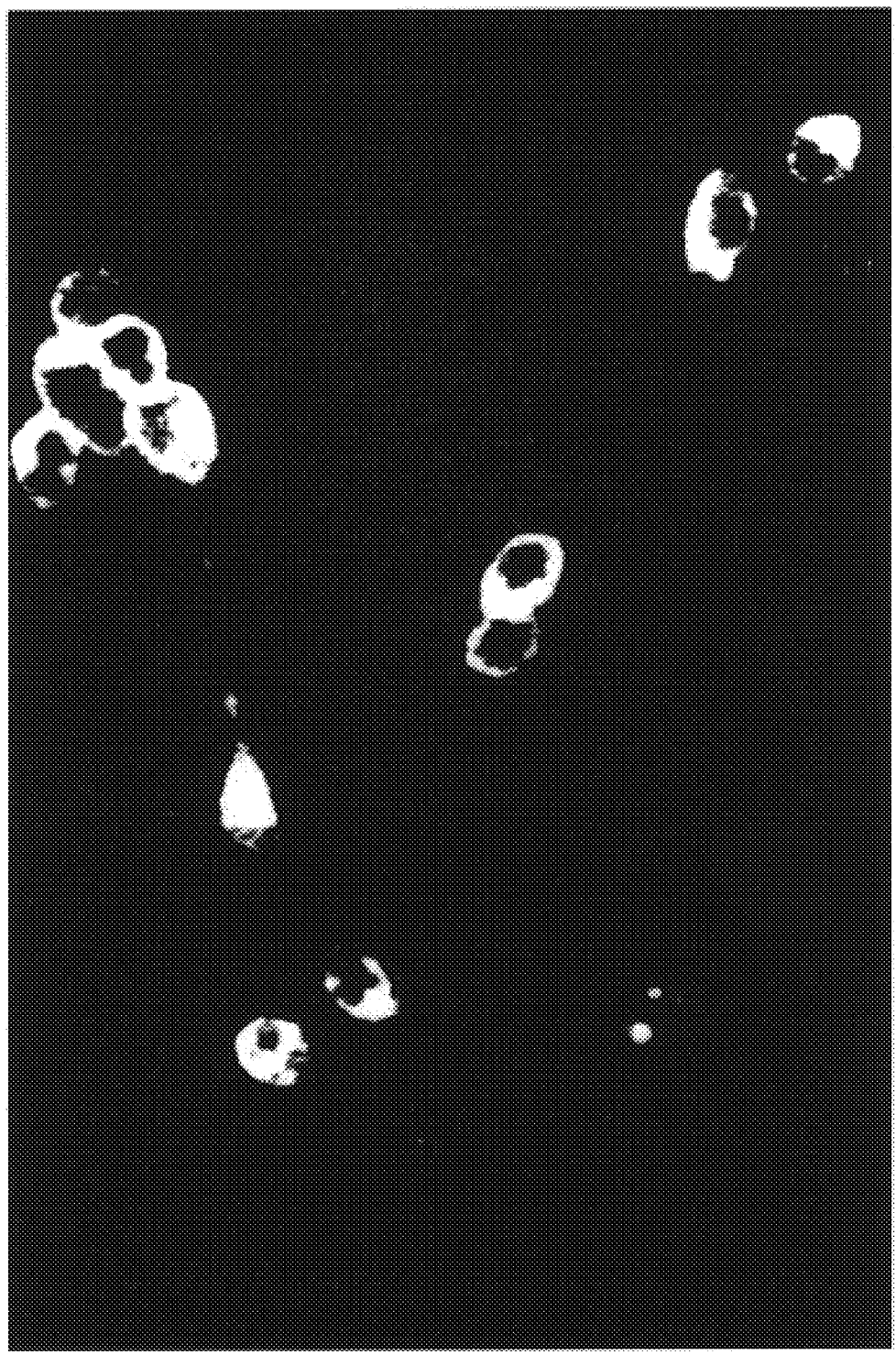

The coverslips were then studied using a Zeiss Laser Microscope, for which a confocal section is shown in FIG. 3B. This localized the bound molecule to the neuronal membrane.

EXAMPLE 7

Additional studies were then carried out to identify the binding molecule, and to confirm its cellular location.

A total mouse brain extract was prepared, by homogenizing murine brains in 50 mM Tris.HCl, pH 7.4, 0.2% sodium deoxycholate, 0.5% Triton X-100, 1 mM aprotinin, 1 mM leupeptin, 1 mM PMSF, and 1 mM benzamidine, which was then centrifuged at 12,000×g for 30 minutes.

A membrane extract was prepared by homogenizing brains in 10 mM Hepes, pH 7.4, 0.5 mM $MgCl_2$, 1 mM aprotinin, 1 mM leupeptin, 1 mM PMSF, and 1 mM benzamidine, followed by centrifugation at 600×g, 15 minutes. Supernatant was then diluted, five times, with the same buffer plus 0.7 mM EDTA, followed by centrifugation over a 0.3 M sucrose cushion at 825×g for 15 minutes. The pellet was resuspended in 1.38 M sucrose, and centrifuged under a 0.3 M sucrose solution at 105,000×g for one hour. The interface was collected and suspended in 20 mM Tris.HCl, pH 7.4, 120 mM NaCl, 1 mM leupeptin, 1 mM PMSF, 1 mM aprotinin, and 1 mM benzamidine.

A cytoplasmic fraction was prepared by homogenizing brain in 50 mM Tris.HCl, pH 7.4, 1.5 mM $MgCl_2$, 10 mM KCl, 1 mM leupeptin, 1 mM pMSF, 1 mM aprotinin, and 1 mM benzamidine, and centrifugation for one hour at 105,000×g. The supernatant served as the cytoplasmic fraction.

Samples from each treatment protocol were resolved by SDS-PAGE, and transferred to a nitrocellulose membrane. Blots were exposed to serum produced as described supra (odd numbered lanes in the figures, as discussed infra), or mouse non-immune serum (even numbered lines, as discussed infra).

Figure 4A:
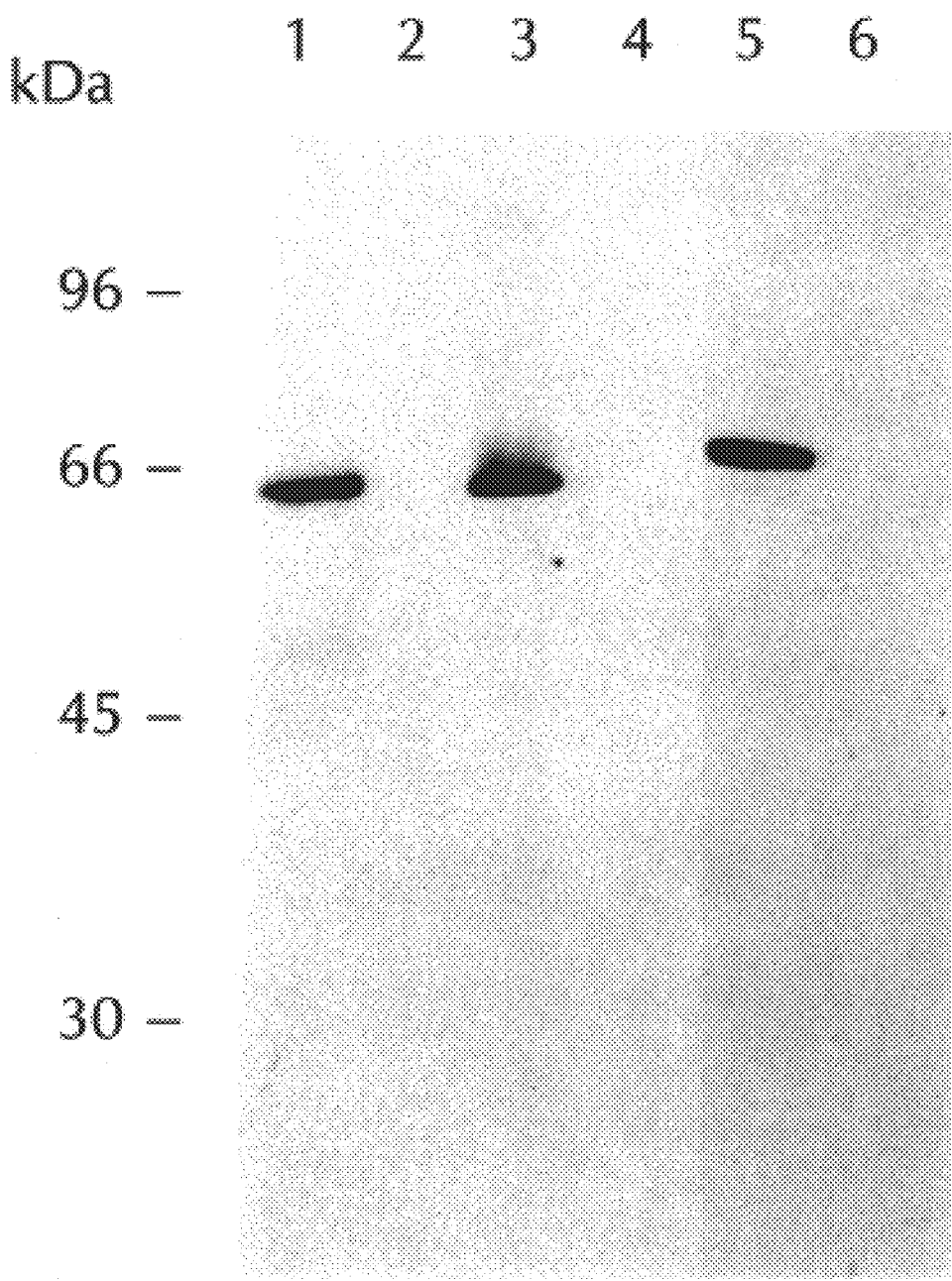
FIGS. 4A and 4B set forth data regarding immunoelectrophotochemical characterization of prion binding proteins.

In FIG. 4A, lanes 1 and 2 show Western blots of total extract; lanes 3 and 4 are Westerns for membrane extracts, and lanes 5 and 6 refer to cytoplasmic extracts. As will be seen, a signal at 60 kDa was found in total brain extracts, and a signal was also found in membrane extracts, but at 63–66 kDa. There was also a detectable species in the cytoplasmic fraction at 60 kDa. See lanes 1, 3 and 5. This suggests that two forms of protein are present in the brain cells, with the membrane bound form being somewhat less prevalent, and thus only detectable in purified fractions. No signal was found when non-immune serum was used.

Figure 4B:
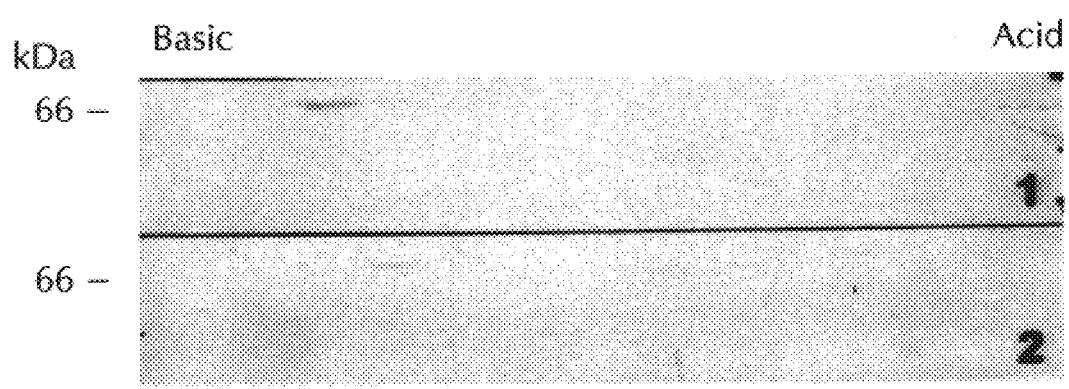

In FIG. 4B, analysis via Western blotting after two dimensional electrophoresis is shown. Extracts were prepared, as described, supra, and were then isolated, in accordance with O'Farrell et al., Cell 12: 1133–1142 (1977), using an ampholyte gradient with light parts at pH 5.0–8.0, and two parts of a ampholite gradient at pH 3.0–10.0 in the first dimension, followed by 10% SDS PAGE under reducing conditions in the second dimension and then transfer to nitrocellulose membranes. Total brain extract is in panel 1, and membrane extract in panel 2. Again, serum prepared as discussed supra was used, followed by anti-mouse IgG, labelled with alkaline phosphatase. Substrate for the enzyme was 5-bromo-4-chloro-3-indolyl phosphate, and nitroblue tetrazolium chloride.

FIG. 4B confirms the molecular weights of 60 and 63–66 kDa, with pIs of 6.9 and 6.8 in total extract. The membrane fraction showed a single component (63–66 kDa, pI 6.8).

EXAMPLE 8

Figure 5:
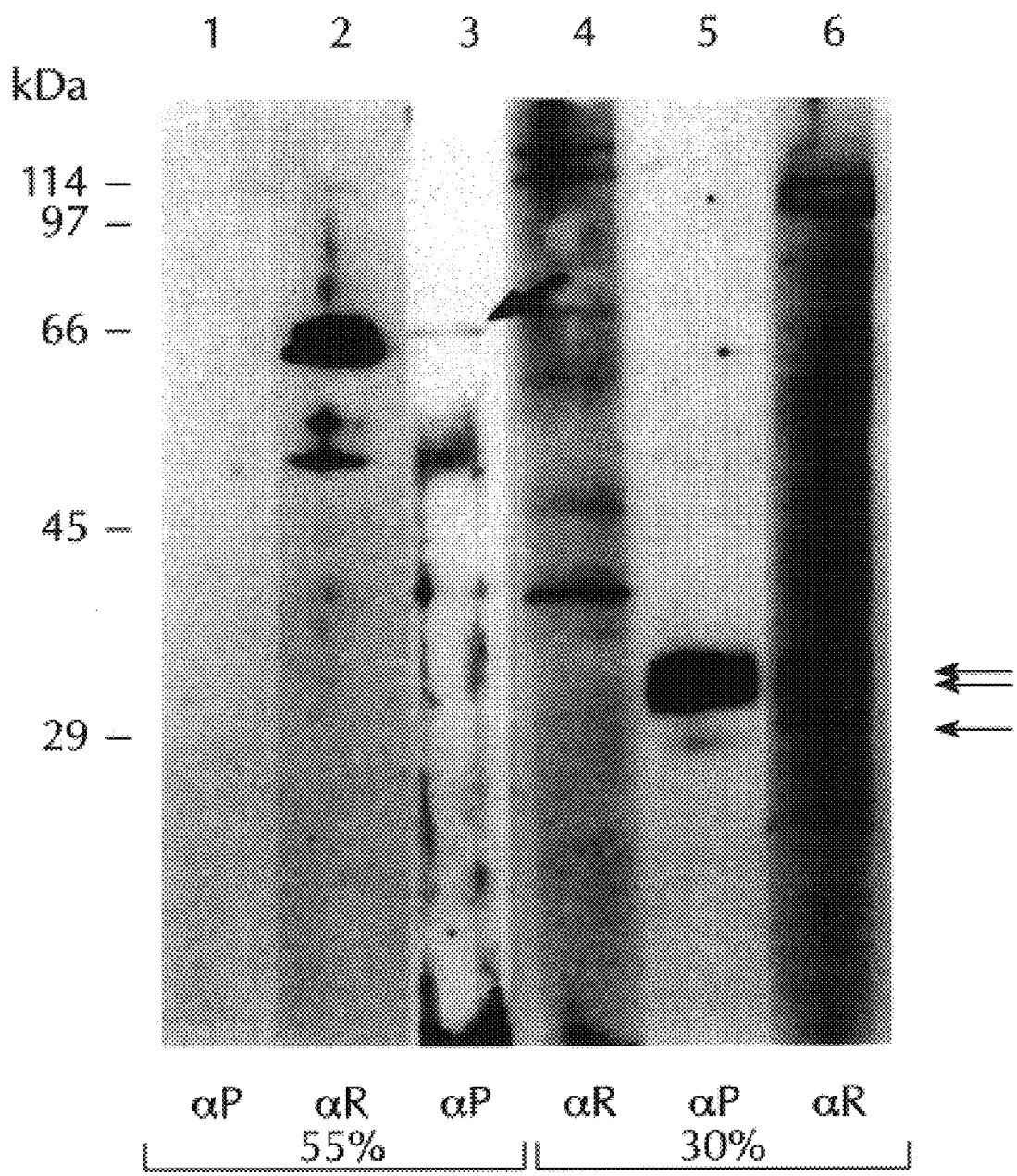
FIG. 5 shows the results of experiments establishing prion binding to complementary protein.

A crucial experiment was to determine if prions bind to the molecules identified supra. To determine this, the total brain extract discussed supra was precipitated, successively, with 30%, 45% and 55% ammonium sulphate. Pellets were dissolved, subjected to SDS-PAGE and then transferred to nitrocellulose membranes. Western blots were then carried out using anti-prion rabbit serum, or serum against the peptide discussed supra. The membranes were developed using enhanced chemiluminescence, and exposed to X-ray film. (The odd numbered lanes of FIG. 5 show the anti-prion rabbit serum work, while the even numbered lanes show the anti-complementary peptide antiserum work). It will be seen that the prion proteins were in the 30% fraction (lane 5), and complementary proteins in the 55% fraction (lane 2). Lane 2 also shows that the fraction precipitated between 45 and 55% ammonium sulphate saturation contained both forms of protein which react with the antiserum against complementary prion peptide. No prion protein was found in the 45–55% fraction, as per lane 1. The fraction shown in lane 5 did not contain material reactive with anti-complementary peptide antiserum. When the 30% fraction was incubated with electrophoretically separated proteins from the 55% fraction, there was detectable reactivity with rabbit anti-prion antiserum, at a 63–66 kDa molecular weight. See lane 3. This indicates that the normal prion protein, i.e., PrPc binds to the heavier form of the molecule, i.e., that found in the membrane. Conversely, when the 55% fraction was incubated with electrophoretic-ally separated proteins of the 30% fraction (lane 6), anti-complementary peptide antibody binding was found, with the binding being to the three known prion isoforms, at 30–33 kDa. Thus, the receptor protein was able to bind to prions in this assays. These assays are referred to as overlay assay. Specifically, in the first one, the solubilized 30% fraction (20 mM Tris.HCl pH 7.4, 120 mM NaCl, 0.05% Tween), was incubated with blots of the 55% fraction on SDS-PAGE. The same solution, but using the 55% fraction, was then applied to the 30% blotted fraction.

The foregoing examples set forth a peptide complementary to a peptide found in PrP. The PrP peptide is known, and is known to be neurotoxic. The inventive peptide, set forth in SEQ ID NO: 1, has been used to develop antibodies which can be used to identify neurons, since the target of the antiserum is specifically nerve cells.

Also a part of the invention are isolated, anti-PrP proteins, also referred to as isolated, PrP binding proteins, which may comprise SEQ ID NO: 1 as part of its amino acid sequence, and which has a molecular weight of from about 55 kilodaltons to about 72 kilodaltons as determined by SDS-PAGE. The proteins, given their ability to bind PrP, are useful diagnostically.

As noted, the isolated 55–72 kD protein may be used to determine PrP in a sample. The methodology involves contacting a sample with a 55–72 kD protein to form complexes therebetween, followed by detection of the thus formed complex. The 55–72 kD proteins may be immobilized, on a bead, column glass tube wall, and so forth, but need not be. If not immobilized, when complexes form in solution, these can be determined by observing migration patterns on a gel, or by way of any of the standard methodologies known to the art. Also, any isolated proteins may be labelled, such as with a chromophore, a radiolabel such as $^{125}I$, an enzyme, or any of the other standard labels used for determining binding. Presence of PrP in a sample may indicate the presence or predisposition toward a prion associated disorder, such as those described supra. These diagnostic assays and systems may be used in the context of animal husbandry, veterinary medicine, and, of course, human pathologies and/or general diagnostic assays.

As noted, the peptide of the invention may be used per se in diagnostic methods, or as an immunogen. In the latter case, it may be coupled to a carrier, such as keyhole limpet hemocyanin, bovine serum albumin, or any of the standard materials used to "haptenize" small peptides. The resulting complexes comprising SEQ ID NO: 1, or the peptide per se, may be formulated in immunogenic compositions, such as with an adjuvant. As noted, the antibodies be they polyclonal in the form of antiserum, e.g., or monoclonal, prepared using standard techniques, which are produced following immunization with the peptides, can be used to detect nerve cells carrying the anti-PrP protein.

It has,also been found that fusion protein of a first protein and prion protein can be made, such as "GST-prion". These fusion proteins are also useful in carrying out assays for anti-prion peptides and proteins, receptors, and so forth.

Other aspects of the invention will be clear to the artisan, and need not be repeated here.

The terms and expressions which have been employed are used as terms of description and not of limitation, and there is no intention in the use of such terms and expressions of excluding any equivalents of the features shown and described or portions thereof, it being recognized that various modifications are possible within the scope of the invention.

What is claimed is:

1. An isolated protein which binds to prion protein, and has a molecular weight of from about 55 kilodaltons to about 72 kilodaltons as determined by SDS-PAGE.

2. The isolated protein of claim 1, comprising the amino acid sequence of SEQ ID NO: 1.

* * * * *